US006511656B2

(12) United States Patent
Candau et al.

(10) Patent No.: US 6,511,656 B2
(45) Date of Patent: *Jan. 28, 2003

(54) COMPOSITIONS FOR COLORING THE SKIN COMPRISING AT LEAST ONE FLAVYLIUM SALT WHICH IS UNSUBSTITUTED IN POSITION 3 AND AT LEAST ONE ORGANOMODIFIED SILICONE

(75) Inventors: Didier Candau, Bievres (FR); Serge Forestier, Claye Souilly (FR); Irène Elguidj, Neuilly (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/901,720

(22) Filed: Jul. 11, 2001

(65) Prior Publication Data

US 2002/0048556 A1 Apr. 25, 2002

(30) Foreign Application Priority Data

Jul. 12, 2000 (FR) .............................. 00 09116

(51) Int. Cl.⁷ .......................... A61K 7/42; A61K 7/44; A61K 7/00
(52) U.S. Cl. ......................... 424/59; 424/60; 424/400; 424/401
(58) Field of Search ........................... 424/59, 60, 400, 424/401

(56) References Cited

U.S. PATENT DOCUMENTS

| 2,463,264 A | 3/1949 | Graenacher et al. |
| 4,247,411 A | 1/1981 | Vanlerberghe et al. |
| 4,367,390 A | 1/1983 | Balleys et al. |
| 4,957,732 A | 9/1990 | Grollier et al. |
| 5,023,327 A | 6/1991 | Yamaoka et al. |
| 5,166,355 A | 11/1992 | Leistner et al. |
| 5,237,071 A | 8/1993 | Leistner et al. |
| 5,585,091 A | 12/1996 | Pelzer et al. |
| 5,643,557 A | 7/1997 | Eteve et al. |
| 5,695,747 A | 12/1997 | Forestier et al. |
| 5,955,060 A | 9/1999 | Hüglin et al. |
| 5,962,452 A | 10/1999 | Haase et al. |
| 5,976,512 A | 11/1999 | Huber |
| 6,074,633 A | 6/2000 | Dubief et al. |
| 6,093,385 A | 7/2000 | Habeck et al. |
| 6,159,455 A | 12/2000 | Habeck et al. |
| 6,177,090 B1 | 1/2001 | Dubief et al. |
| 6,238,649 B1 | 5/2001 | Habeck et al. |
| 6,241,785 B1 | 6/2001 | Darmenton et al. |

FOREIGN PATENT DOCUMENTS

| CN | 1064284 A | 9/1992 |
| CN | 1035512 C | 7/1997 |
| DE | 197 26 184 | 12/1998 |
| DE | 197 55 649 | 6/1999 |
| DE | 198 55 649 | 6/2000 |
| EP | 0 219 830 | 4/1987 |
| EP | 0 342 834 | 11/1989 |
| EP | 0 517 104 | 12/1992 |
| EP | 0 518 772 | 12/1992 |
| EP | 0 518 773 | 12/1992 |
| EP | 0 570 838 | 11/1993 |
| EP | 0 669 323 | 8/1995 |
| EP | 0 775 698 | 5/1997 |
| EP | 0 787 469 | 8/1997 |
| EP | 0 796 615 | 9/1997 |
| EP | 0 796 851 | 9/1997 |
| EP | 0 822 202 | 2/1998 |
| EP | 0 863 145 | 9/1998 |
| EP | 0 878 469 | 11/1998 |
| EP | 0 893 119 | 1/1999 |
| EP | 0 933 376 | 8/1999 |
| EP | 0 967 200 | 12/1999 |
| EP | 0 852 488 | 8/2001 |
| FR | 2 315 991 | 1/1977 |
| FR | 2 416 008 | 8/1979 |
| FR | 2 589 476 | 7/1987 |
| FR | 2 641 185 | 6/1990 |
| FR | 2 757 383 | 6/1998 |
| GB | 2 303 549 | 2/1997 |
| WO | WO 93/04665 | 3/1993 |
| WO | WO 93/23579 | 11/1993 |
| WO | WO 98/20883 | 5/1998 |

OTHER PUBLICATIONS

Co–pending Application No. 09/901,725; Attorney Docket No. 05725.0937 Title: Composition Comprising at Least One Self–Tanning Agent Chosen from Monocarbonyl and Polycarbonyl Compounds and a Flavylium Salt Compound which is Unsubstituted in Position 3, for Coloring the Skin, and Uses Thereof. Inventors: Didier Candau et al. U.S. Filing Date: Jul. 11, 2001.

(List continued on next page.)

Primary Examiner—Shelley A. Dodson
(74) Attorney, Agent, or Firm—Finnegan, Henderson, Farabow, Garrett & Dunner, L.L.P.

(57) ABSTRACT

Methods for manufacturing cosmetic and dermatological compositions for coloring the skin; and composition, for example, an emulsion, comprising (1) at least one aqueous phase, (2) at least one fatty phase, (3) at least one flavylium salt which is unsubstituted in position 3; which is substituted with at least one radical chosen from hydroxyl and alkoxy radicals; and which is, for example, obtained at least one of synthetically, from a plant extract, and from an enriched plant extract, in an amount which is effective for artificially coloring the skin, for example, effective for obtaining, 30 minutes after application of the emulsion to a fair skin in an amount of 2 mg/cm², a darkening of the skin color characterized in the L*a*b* colorimetric measuring system by a ΔL* ranging from −0.5 to −20, and (4) at least one organomodified silicone, where the emulsion is configured as at least one of a cosmetic and a dermatological emulsion.

77 Claims, No Drawings

OTHER PUBLICATIONS

Co-pending Application No. 09/901,724; Attorney Docket No. 05725.0938 Title: Compositions Comprising at Least One UV Screening Agent and At Least One Flavylium Salt Which is Unsubstituted in Position 3, For Coloring the Skin, and Uses Thereof. Inventors: Didier Candau et al. U.S. Filing Date: Jul. 11, 2001.

David Doig Pratt et al., "A Synthesis of Pyrylium Salts of Anthocyanidin Type. Part II,", Journal of The Chemical Society, vol. CXXIII, 1923, pp. 745–757.

Alexander Robertson et al., "A Synthesis of Pyrylium Salts of Anthocyanidin Type. Part IX. Some Hydroxyflavylium Salts," Journal of The Chemical Society, Jul. 1926, pp. 1951–1959.

Alexander Robertson et al., "A Synthesis of Pyrylium Salts of Anthocyanidin Type. Part XIV," Journal of The Chemical Society, 1927, pp. 2196–2206.

Alexander Robertson et al., "Snythesis of Pyrylium Salts of Anthocyanidin Type. Part XV. The Synthesis of Cyanidin Chloride by Means of O–Benzoylphloroglucinaldehyde," Journal of The Chemical Society, 1928, pp. 1526–1532.

J J.G. Sweeny et al., "Synthesis of Anthocyanidins—The Oxidative Generation of Flavylium Cations Using Benzoquinones," Tetrahedron, vol. 33, 1977, pp. 2923–2926.

Janet C. Bell et al., "Experiments on the Synthesis of Anthocyanins. Part XX. Synthesis of Malvidin 3–Galactoside and its Probable Occurence as a Natural Anthocyanin," Journal of The Chemical Society, 1934, pp. 813–818.

A.D. Bangham et al., "Diffusion of Univalent Ions Across the Lamellae of Swollen Phospholipids," Journal of Molecular Biology, vol. 13, No. 1, Aug. 1965, pp. 238–252.

A. Chardon et al., "Skin Colour Typology and Suntanning Pathways," International Journal of Cosmetic Science, vol. 13, No. 4, pp. 191–208.

English language Derwent Abstract of DE 197 26 184, Dec. 24, 1998.

English language Derwent Abstract of CN 1064284 A, Sep. 9, 1992.

English language Derwent Abstract of FR 2 315 991, Jan. 28, 1977.

English language Derwent Abstract of FR 2 589 476, Jun. 27, 1990.

COMPOSITIONS FOR COLORING THE SKIN COMPRISING AT LEAST ONE FLAVYLIUM SALT WHICH IS UNSUBSTITUTED IN POSITION 3 AND AT LEAST ONE ORGANOMODIFIED SILICONE

The present invention can relate to an emulsion, such as, for example, a cosmetic and/or dermatological emulsion, comprising:

at least one aqueous phase at least one fatty phase;

at least one flavylium salt compound which is unsubstituted in position 3, substituted with at least one radical chosen from hydroxyl and alkoxy radicals, and, for example, obtained from at least one of synthetically, from a plant extract, and from an enriched plant extract, and, for example, in an amount effective for obtaining, 30 minutes after application to a fair skin, a darkening of the skin color characterized in the L*a*b* calorimetric measuring system by a ΔL* ranging from −0.5 to −20; and at least one organomodified silicone.

Nowadays, it can be important and/or desirable to look healthy and a tanned skin is always a sign of good health. However, a natural tan may not always desirable since it may require prolonged exposure to UV radiation, for example, UV-A radiation which can causes the tanning of the skin but, however, may induce an adverse change therein, in particular in the case of sensitive skin and/or of skin which is continually exposed to solar radiation. It is thus can be desirable to find an alternative to a natural tan which is compatible with the requirements of such skin types.

Cosmetic products intended for artificially tanning the skin may be based on carbonyl derivatives which, by interacting with the amino acids in the skin, can allow the formation of colored products.

To this end, dihydroxy-acetone (DHA) can be used in cosmetics as an agent for artificially tanning the skin; when applied to the skin, for example, to the face, it can give a tanning or bronzing effect which is similar in appearance to that which may result from prolonged exposure to sunlight (a natural tan) or to a UV lamp.

Drawbacks of DHA can include the length of time it can take for the coloration to develop. For example, several hours (3 to 5 hours in general) can be required for the coloration to be revealed. Thus, there is an increasing demand for self-tanning products that are at least one of fast-acting and give a coloration closer to that of a natural tan.

Efforts are continually being made to find novel compounds and novel compositions which can give the skin an artificial coloration, for example, close to that of a natural tan in at least one of a simple, effective, fast and risk-free manner.

Anthocyanin colorants have been known for a long time as pharmaceutical and food colorants. These anthocyans may be present in nature in the form of heterosides, known as anthocyanosides, and genins, known as anthocyanidines. These anthocyans include phenyl-2-benzopyrylium derivatives and flavylium derivatives and may be present, for example, in plants in the form of salts. Anthocyans may be red-, violet- or blue-colored compounds which can color flowers, fruit, and occasionally leaves. The color observed may depend both on the structure of the predominant genin and on the conditions of the medium in which the anthocyanin colorants are present.

Now, after considerable research conducted in the field of artificial dyeing of the skin, the Inventors have discovered that particular emulsions comprising, as skin-coloring agent, at least one flavylium salt compound which is unsubstituted in position 3 and is substituted with at least one radical chosen from hydroxyl and alkoxy radicals, and at least one organomodified silicone, can make it possible to give skin an artificial coloration, for example, close to that of a natural tan, where the coloration can at least be one of provided immediately and/or in short period of time, good stability, and cosmetically pleasant.

One embodiment of the present invention is an emulsion, such as, for example, at least one of a cosmetic and a dermatological emulsion, comprising:

(a) at least one aqueous phase;

(b) at least one fatty phase;

(c) at least one flavylium salt compound which is unsubstituted in position 3, substituted with at least one radical chosen from hydroxyl and alkoxy radicals, and, for example, obtained at least one of synthetically, from a plant extract, and from an enriched plant extract, and, for example, in an amount effective for obtaining, 30 minutes after application to a fair skin, a darkening of the skin color characterized in the L*a*b* calorimetric measuring system by a ΔL* ranging from −0.5 to −20; and (d) at least one organomodified silicone. The flavylium salt may be present in the emulsion in an amount effective for delivering 2 mg/cm$^2$ upon application to the skin.

As used herein, the expressions "cosmetic or dermatological emulsion," "cosmetic emulsion," "dermatological emulsion," and grammatical variants thereof refer to any emulsion whose aqueous phase and fatty phase comprise substances that are at least one of cosmetically and/or dermatologically acceptable for topical application to the skin.

According to certain embodiments, the present invention comprises a method of providing skin with an artificial coloration, for example, close to that of a natural tan, comprising the use of at least one flavylium salt compound which is unsubstituted in position 3, substituted with at least one radical chosen from hydroxyl and alkoxy radicals, and, for example, obtained at least one of synthetically, from a plant extract, and from an enriched plant extract, and the use of at least one organomodified silicone, in a cosmetic and/or dermatological composition.

According to certain embodiments, the present invention comprises a process for giving the skin an artificial coloration, such as close to that of a natural tan, comprising applying to the skin a cosmetic composition comprising an effective amount of at least one flavylium salt compound which is unsubstituted in position 3, substituted with at least one radical chosen from hydroxyl and alkoxy radicals, and, for example, obtained at least one of synthetically, from a plant extract, and from an enriched plant extract; and of at least one organomodified silicone.

According to certain embodiments, the present invention comprises using an emulsion to manufacture cosmetic compositions for coloring the skin.

According to certain embodiments, the present invention comprises including an organomodified silicone in a cosmetic and/or dermatological emulsion comprising at least one flavylium salt compound which is unsubstituted in position 3, and which is substituted with at least one radical chosen from hydroxyl and alkoxy radicals. The emulsion may be used, for example, to at least one of obtain an immediate or relatively rapid coloration of the skin, provide good physical stability to the composition, and be cosmetically pleasant.

According to certain embodiments, the compositions and uses in accordance with the present invention can make it possible to obtain an artificial coloration close to that of a natural tan in a short space of time. Thus, an immediate or short time coloration is obtained, which can allow the application to be visualized and consequently can allow more uniform spreading of the composition on the skin and thus of the resulting coloration.

As used herein, the expressions "composition intended for artificially coloring the skin," "emulsions intended for artificially coloring the skin," and grammatical variants thereof are understood to mean formulations with will be understood to mean a formulation with a particular affinity for the skin which allows it to give the skin a long-lasting coloration, which may be at least one of non-covering (that is to say which does not have a tendency to opacify the skin), not removed with at least one of water and solvents, and able to withstand both rubbing and washing with a solution containing surfactants. Such a long-lasting coloration may thus be distinguished from the superficial and transient coloration provided, for example, by a make-up product.

In accordance with the generally accepted definition, the term "silicone" is understood to mean any organosilicone polymer or oligomer chosen from linear, cyclic, branched, and crosslinked structures, of variable molecular weight, obtained, for example, by polymerization and/or polycondensation of suitably functionalized silanes, and comprising a repetition of main units in which the silicon atoms are linked together via oxygen atoms (siloxane bond ≡Si—O—Si≡), optionally substituted hydrocarbon-based radicals being directly linked via a carbon atom to the said silicon atoms. The hydrocarbon-based radicals that can be used include, for example, alkyl radicals, such as, for example, $C_1$–$C_{10}$ alkyl radicals, such as, for example, methyl radicals; fluoroalkyl radicals; and aryl radicals, such as, for example, phenyl radicals. Silicones are defined in greater detail in the book by Walter Noll "Chemistry and Technology of Silicones" (1968) Academie Press, the disclosure of which directed to silicones is incorporated herein by reference.

Other characteristics, aspects and advantages at least one of which may be present in a specific embodiment, of the present invention will become apparent on reading the detailed description which follows.

The at least one organomodified silicone which may be used in accordance with the invention are silicones as defined above and comprising in their structure at least one organofunctional groups attached via a hydrocarbon-based radical. The at least one organomodified silicones which may be used in accordance with the invention may be in the form of, for example, at least one of oils, waxes, resins, and gums. They may be wholly or partially water-soluble or water-insoluble.

The at least one organomodified silicones may be, for example, chosen from, for example, polyorganosiloxanes comprising at least one of:

(1) oxyalkylenated (such as, for example, at least one of oxyethylenated and oxypropylenated) groups, including, for example, those disclosed in patent application EP-0 796 615, the disclosure of which directed to said groups and silicones is incorporated herein by reference, and corresponding to the following formula (I) and (II):

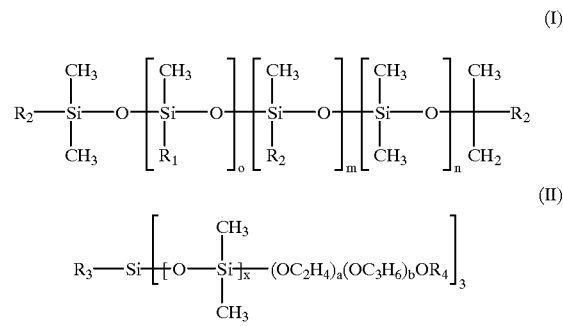

where:
each R1, which may be identical or different, is chosen from linear and branched $C_1$–$C_{30}$ alkyl radicals, and phenyl radicals, each R2, which may be identical or different, is chosen from $C_cH_{2c}$—(—O—$C_2H_4$)a—(—O—$C_3H_6$)$_b$—(O—$C_4H_8$)$_d$—R$_5$, each $R_3$ and each $R_4$, which may be identical or different, is chosen from linear and branched $C_1$–$C_{12}$ alkyl radicals, such as, for example, a methyl radical, each $R_5$, which may be identical or different, is chosen from a hydrogen atom, a hydroxyl radical, linear and branched alkyl radicals comprising from 1 to 12 carbon atoms, linear and branched alkoxy radicals comprising from 1 to 6 carbon atoms, linear and branched acyloxy radicals comprising from 2 to 12 carbon atoms, $NHCH_2CH_2COOM$, aminoalkyls optionally substituted on the amine, carboxy ($C_1$–$C_{30}$)acyl, optionally substituted phosphono groups, —O—CO—($CH_2$)d-$CO_2M$, —NHCO($CH_2$)$_d$OH, and —$NH_3Y$, each M, which may be identical or different, is chosen from a hydrogen, Na, K, Li, $NH_4$, and organic amines, a ranges from 0 to 50, b ranges from 0 to 50, with the proviso that the sum of a+b is greater than or equal to 1, c ranges from 0 to 4, d ranges from 0 to 10, m ranges from 0 to 20, n ranges from 0 to 500, o ranges from 0 to 20, x ranges from 1 to 100, Y is chosen from mineral and organic monovalent anions, such as, for example, halides (such as, for example, chloride and bromide), sulphate and carboxylate (such as, for example, acetate, lactate or citrate);

such as, for example, those sold under the trade names FLUID DC 193 by the company Dow Corning, SILWET L 77 by the company OSI and MAZIL 756 by the company Mazer PPG; mention may also be made of the products sold under the names "SILICONE DC 3225C" and "DC Q2-5200" by the company Dow Corning;

(2) alkoxy groups, such as, for example, the products sold under the name "Silicone Copolymer F-755" by SWS Silicones and ABIL WAX 2428, 2434 and 2440 by the company Goldschmidt;

(3) anionic groups such as, for example, 2-hydroxyalkylsulphonate and 2-hydroxyalkylthiosulphate, such as, for example, the products sold by the company Goldschmidt under the names "ABIL S201" and "ABIL S255";

(4) thiol groups, such as, for example, the products sold under the names "GP 72 A" and "GP 71" by Genesee;

(5) anionic groups of the carboxylic type, such as, for example, the organomodified silicones disclosed in patent applications WO 95/23579, EP-A-0 219 830, and WO 98/20883, the disclosures of which directed to said groups and silicones are incorporated herein by reference, such as, for example, those corresponding to formula (III) below:

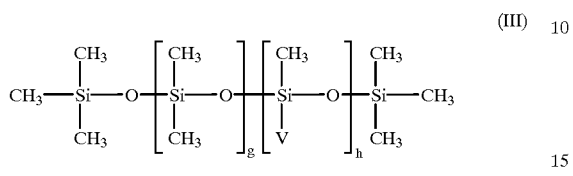

(III)

where V is chosen from a radical of the formula —($R^1O$)$_e$—$R^2$—($OR^3$)$_f$—COOM, in which:
$R^1$ and $R^3$ are each independently chosen from linear and branched alkylene radicals comprising from 2 to 20 carbon atoms,
each $R^2$ is chosen from linear and branched alkylene radicals comprising from 1 to 50 carbon atoms and optionally at least one hydroxyl group,
e is a number chosen from 0 and 1,
f is a number ranging from 0 to 200,
M is chosen from hydrogen, alkalimetal and an alkaline-earth metals, $NH_4$ and quaternary ammonium group such as, for example, mono-, di-, tri- and tetra($C_1$-$C_4$ alkyl) ammonium groups,
h is a number ranging from 1 to 1000,
g is a number ranging from 0 to 1000,
with the proviso that the sum g+h can optionally range from 2 to 1000;
for example those sold under the name HUILE M 642 by the company Wacker, under the names SLM 23 000/1 and SLM 23 000/2 by the company Wacker, under the name 176-12057 by the company General Electric, under the name FZ 3703 by the company OSI, and under the name BY 16 880 by the company Toray Silicone; mention may also be made of the products disclosed in patent EP 186 507, the disclosure of which directed to said groups and silicones is incorporated herein by reference, from the company Chisso Corporation, and of the alkylcarboxylic type, such as those present in the product X-22-3701E from the company Shin-Etsu;

(6) hydroxylated groups, such as, for example, polyorganosiloxanes comprising a hydroxyalkyl function, such as, for example, those disclosed in French patent application FR-A-85 16334, the disclosure of which directed to said groups and silicones is incorporated herein by reference, corresponding to the following formula (IV):

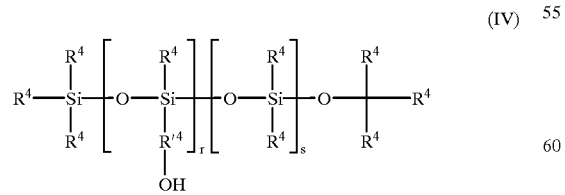

(IV)

where:
each $R^4$, independently, is chosen from methyl and phenyl radicals, with the proviso that at least 60 mol % of the radicals $R_4$ are chosen from methyl radicals;

each $R'^4$, independently, is chosen from divalent hydrocarbon-based $C_2$-$C_{18}$ alkylene chain units,
r is a number ranging from 1 and 30, and
s is a number ranging from 1 and 150;

(7) acyloxyalkyl groups such as, for example, polyorganosiloxanes disclosed in French patent application FR-A-2 641 185, the disclosure of which directed to said groups and silicones is incorporated herein by reference, and corresponding to the following formula (V):

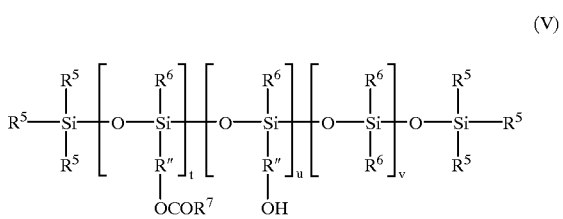

(V)

in which:
each $R^5$ is, independently, chosen from methyl, phenyl, —$OCOR_5$, and hydroxyl groups, with the proviso the proviso that not more than one of the radicals $R_5$ attached to one silicon atom is chosen from hydroxyl,
each R" is, independently, chosen from linear and branched divalent hydrocarbon-based $C_2$-$C_{18}$ alkylene radicals,
each $R^6$ is, independently, chosen from methyl and phenyl, with the proviso that at least 60 mol % of all of the radicals $R^5$ and $R^6$ are chosen from methyl groups,
each $R^7$ is, independently, chosen from $C_8$-$C_{20}$ alkyl and alkenyl groups;
v is a number ranging from 1 to 120,
u is a number ranging from 1 to 30,
t is a number ranging from 0 to less than the value of 0.5 u,
with the proviso that the value of t+u ranges from 1 to 30;
with the proviso that the polyorganosiloxanes of formula (V) may contain at least one group of the following formula:

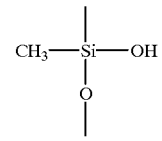

in a proportion not exceeding 15% of the sum t+u+v;

(8) substituted and unsubstituted amine groups such as, for example, the silicones disclosed in patent application EP-A-0 852 488, the disclosure of which directed to said groups and silicones is incorporated herein by reference, such as aminosilicones chosen from:
(a) polysiloxanes corresponding to the following formula (VI):

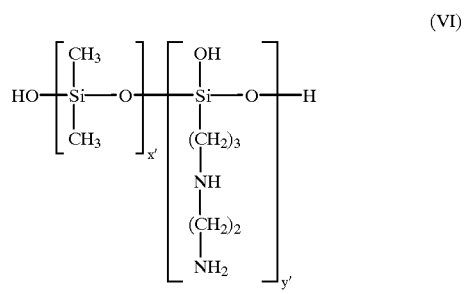

(VI)

in which x' and y' are integers dependent on the molecular weight, and, for example, can be chosen such that the number-average molecular weight ranges from 5000 to 500,000, and, for example, y' can be an integer greater than or equal to 1;
(b) cationic silicone polymers corresponding to the following formula (VII):

$$R^8{}_iG_{3-i}-Si(OSiG_2)_k-(OSiG_jR^8{}_{2-j})_l-O-SiG_{3-i}-R^8{}_i \quad (VII)$$

in which:
G is chosen from a hydrogen atom and phenyl, OH, and $C_1$–$C_8$ alkyl groups, such as, for example methyl,
i is a chosen from the number 0 and an integer ranging from 1 to 3,
j is a number chosen from 0 and 1,
k and l are numbers chosen such that the sum (k+l) ranges from 1 to 2000, such as, for example, ranging from 50 to 150, with k optionally be chosen from a number ranging from 0 to 1999, such as, for example, from 49 to 149 and l optionally being chosen from a number ranging from 1 to 2000, such as, for example, from 1 to 10,
with the proviso that at least one of i and l are greater than or equal to 1,
$R_8$ is chosen from monovalent radicals of formula —$C_qH_{2q}L$ in which q is a number ranging from 2 to 8 and L is an optionally quaternized amine group chosen from groups:
—$NR^9$—$CH_2$—$CH_2$—$N(R^9)_2$,
—$N(R^9)_2$,
—$N^{\oplus}(R^9)_3A^-$, and
—$N^{\oplus}(R^9)$—$CH_2$—$CH_2$—$N^{\oplus}R^9H_2A^-$,
in which $R^9$ is chosen from hydrogen, phenyl, benzyl, and saturated monovalent hydrocarbon-based radicals, such as, for example an alkyl radical comprising from 1 to 20 carbon atoms, and $A^-$ is chosen from halide ions such as, for example, fluoride, chloride, bromide, and iodide;
(c) the cationic silicone polymers corresponding to the formula:

(VIII)

$$R^{10}-\underset{\underset{R^{10}}{|}}{\overset{\overset{R^{10}}{|}}{Si}}-O-\left[\underset{\underset{R_{11}}{|}}{\overset{\overset{R_{10}}{|}}{Si}}-O\right]_w-\left[\underset{\underset{R^{10}}{|}}{\overset{\overset{R^{10}}{|}}{Si}}-O\right]_z-\underset{\underset{R^{10}}{|}}{\overset{\overset{R^{10}}{|}}{Si}}-R^{10}$$

with side chain: $CH_2$—$CHOH$—$CH_2$—$^+N(R^{10})_3Q^-$ in which:
$R^{10}$ is chosen from monovalent hydrocarbon-based radicals comprising from 1 to 18 carbon atoms, such as, for example, $C_1$–$C_{18}$ alkyl $C_2$–$C_{18}$ alkenyl radicals, such as, for example, methyl,
$R^{11}$ is chosen from divalent hydrocarbon-based radicals, such as, for example, $C_1$–$C_{18}$ alkylene and divalent $C_1$–$C_{18}$ alkyl radicals, such as, for example $C_1$–$C_{18}$ alkylenoxy radicals,
$Q^-$ is a halide ion, such as, for example, chloride,
w represents an average statistical value, and is chosen from a number ranging from 2 to 20, such as, for example, from 2 to 8,
z represents an average statistical value, and is chosen from a number ranging from 20 to 200, such as, for example, from 20 to 50; by way of example of aminosilicones, mention may be made of the products sold under the name GP 4 SILICONE FLUID and GP 7100 by the company Genesee and the products sold under the names Q2 8220 and DOW CORNING 929 and 939 by the company Dow Corning;

(9) hydroxyacylamino groups, such as, for example, the polyorganosiloxanes disclosed in patent application EP 342 834, the disclosure of which directed to said groups and silicones is incorporated herein by reference. Mention may be made, for example, of the product Q2-8413 from the company Dow Corning; and

(10) optionally substituted aryl groups, such as, for example, phenyl, naphthyl, benzyl, and phenethyl groups, such as, for example, the non-volatile arylsilicones disclosed in patent application EP-A-822 202, the disclosure of which directed to said groups and silicones is incorporated herein by reference; as examples of these compounds, mentioned may be made of those sold by the company Bayer under the name HUILE BAYSILONE FLUID PD5, by the company Dow Corning under the name DOW CORNING 556 FLUID, by Rhône-Poulenc under the names MIRASIL DPDM, RHODORSIL HUILE 510 V 100, RHODORSIL HUILE 550, RHODORSIL HUILE 510V500, and RHODORSIL HUILE 710, and under the names WACKER BELSIL PDM 20, PDM 200 and PDM 1000 by the company Wacker.

The at least one organomodified silicone may be present in an amount ranging, for example, from 0.1% to 40%, such as, for further example, from 0.5% to 20%, relative to the total weight of the composition.

The at least one flavylium salt can be chosen from, for example, compounds of formula (1) below:

(1)

[flavylium salt structure with substituents $R^{12}$, $R^{13}$, $R^{14}$, $R^{15}$ and counterion $X^-$]

in which:
$R^{12}$ is chosen from an OH radical, and linear and branched, saturated and unsaturated $C_2$–$C_8$ alkoxy radicals,
$R^{13}$, $R^{14}$, and $R^{15}$, which may be identical or different, are each chosen from H and $R^{12}$, with the proviso that at least one of the radicals $R^{12}$, $R^{13}$, $R^{14}$, and $R^{15}$ is chosen from OH,
$X^-$ is chosen from organic and mineral anions. For example, $X^-$ can be chosen from an anion derived from a mineral acid derivative, and can be chosen from, for example, halides, such as, for example, bromide and chloride. As another example, $X^-$ can be chosen from an anion derived from an organic acid, and can be chosen from, for example, acetate, borate, citrate, tartrate, lactate, bisulphate, sulphate, and phosphate.

According to certain embodiments, the at least one flavylium salt can be chosen from compounds of formula (1) in which $R^{12}$ is chosen from OH and $OCH_3$.

According to certain embodiments, the at least one flavylium salt can be chosen from salts, such as chloride salts, of the following:
4',5,7-trihydroxyflavylium, the chloride salt being commonly known as "apigeninidine chloride",
3',4',7-trihydroxyflavylium,
4'-hydroxyflavylium,
4',7-dihydroxyflavylium,
3',4'-dihydroxyflavylium,
3',4'-dihydroxy-7-methoxyflavylium,
3',4',5,7-tetrahydroxyflavylium, and
3',4',5',5,7-pentahydroxyflavylium.

For example, the at least one flavylium salt may be chosen from at least one of apigeninidine chloride (4',5,7-trihydroxyflavylium chloride) and 3',4',7-trihydroxyflavylium.

According to certain embodiments, the present invention comprises using apigeninidine chloride in the form of, or derived from, a plant extract, which can be readily prepared by extraction and isolation from leaves of *Sorghum caudatum* according to, for example, at least one of the processes disclosed in patents CN 1,064,284A and CN 1,035,512C, the disclosures in both patents directed to said extraction and/or isolation are hereby incorporated by reference, and variants of these processes.

According to certain embodiments, the at least one flavylium salt may be chosen from those extracted from at least one of the stems, seeds, and leaves of *Sorghum bicolour*; the petals of *Gesneria fulgens*; and at least one of the species *Blechum procerum* and Sorghum in combination with *Colletotrichum graminicola*.

According to certain embodiments, the present invention comprises using an extract from the leaves of *Sorghum bicolour*, which can be obtained by an aqueous-alcoholic extraction in acidic medium at an extraction temperature ranging from 30 to 40° C. with a ratio of the volume of solvent to the volume of *Sorghum bicolor* leaves ranging from 10 to 30. The Sorghum plant extract can have an approximate titre ranging from 0.05% to 50% by weight of apigeninidine chloride.

The at least one flavylium salt compound which is unsubstituted in position 3 and which is substituted with at least one radical chosen from hydroxyl and alkoxy radicals, may be readily and/or cheaply obtained by synthesis, such as, for example, the well-known method of R. Robinson and D. Pratt, J. Chem. Soc. 745 (1923), the disclosure of which directed to said synthesis is hereby incorporated by reference. The method comprises condensing at least one of an ortho-hydroxybenzaldehyde and a substituted ortho-hydroxybenzaldehyde with at least one of an acetophenone and a substituted acetophenone to yield, by selecting the substituents, a desired at least one flavylium salt compound, corresponding to formula (1).

Taking apigeninidine chloride (4',5,7-trihydroxyflavylium chloride) as an example, the synthetic scheme (i) may be as follows:

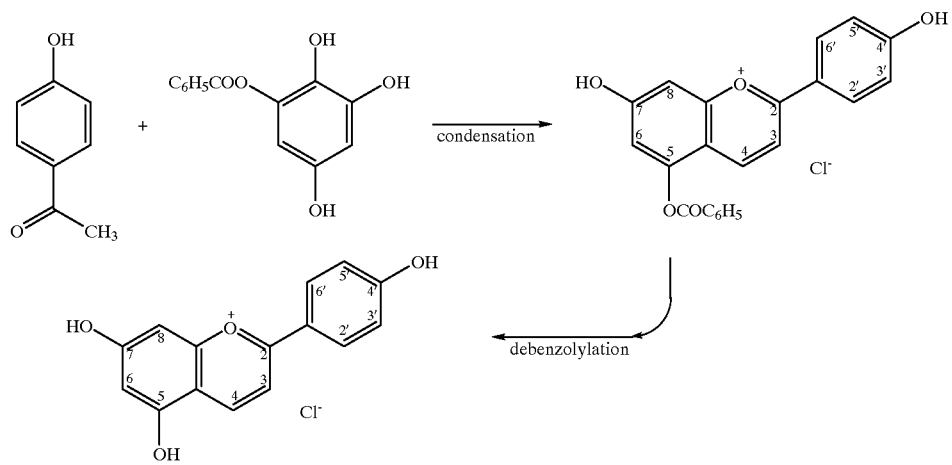

Taking 3',4',7-trihydroxyflavylium chloride as an example, the synthetic scheme (ii) may be as follows:

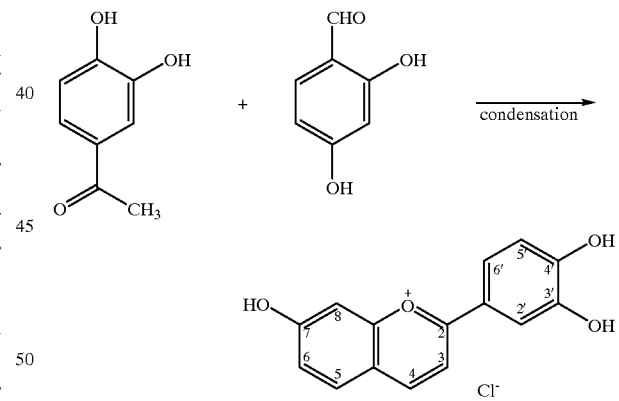

A variety of synthetic routes, such as those that are well known in the field, may be used to lead to apigeninidine.

One method for preparing apigeninidine comprises, for example, in a first step, preparing trimethylapigeninidine by condensing commercial 4,6-dimethoxy-2-hydroxybenzaldehyde with commercial 4-methoxyacetophenone in an anhydrous ether medium at 0° C., and saturating with anhydrous HCl, to yield, after filtration, an orange-red precipitate of trimethylapigeninidine. In a second step, the trimethylapigeninidine obtained in the preceding step is hydrolysed to apigeninidine chloride, the reaction being carried out in a medium of HI and phenol and AgCl dissolved in methanol. Such a synthetic method is disclosed for example, by R. Robinson and A. Robertson in J. Chem. Soc. 1951 (1926) and 2196 (1927), the disclosure of which directed to said synthesis is incorporated herein by reference.

Another method, for example, for preparing apigeninidine comprises condensing 2,4,6-trihydroxybenzaldehyde with 4-hydroxyacetophenone at 0° C. in an anhydrous solvent medium, for example ethyl acetate, and saturating with anhydrous HCl, to yield apigeninidine chloride. Such a method is disclosed, for example, by R. Robinson and A. Robertson in J. Chem. Soc. 1528 (1928), the disclosure of which directed to said synthesis is hereby incorporated by reference.

Another method, for example, for preparing apigeninidine chloride comprises reducing at least one of a flavone, naringenin, and triacetyl derivatives thereof, with $NaBH_4$, and then oxidizing the product obtained with chloranil (tetrachloro-1,4-benzoquinone). The method is disclosed, for example, by J. G. Sweeny and G. A. Iacobucci in the review Tetrahedron 33 2923–2927 (1977), the disclosure of which directed to said synthesis is hereby incorporated by reference.

As a further example, use may be made of a method comprising condensing 2,4-dihydroxy-6-benzoyloxybenzaldehyde with 4-hydroxyacetophenone at 0° C. in an anhydrous ethyl acetate medium, saturating with anhydrous HCl and then debenzoylating the product obtained with sodium hydroxide, to yield apigeninidine chloride in high yield, according to scheme (i) described above can. The method is disclosed, for example, by R. Robinson and J. C. Bell in J. Chem. Soc. 813 (1934), the disclosure of which directed to said synthesis is hereby incorporated by reference.

The concentration of the at least one flavylium salt compound as described according to the present invention may range, for example, from about 0.0001% to 10%, such as, for example, from 0.001% to 5%, by weight relative to the total weight of the composition.

According to certain embodiments, the present invention is directed to compositions that can provide, 30 minutes after application to a fair skin in an amount of 2 $mg/cm^2$, a darkening characterized in the (L*, a*, b*) colorimetric measuring system by a ΔL* ranging from −0.5 to −20. For example, ΔL* may range from −0.5 to −1.

According to certain embodiments, the present invention is directed to compositions that can provide, 30 minutes after application to the skin in an amount of 2 $mg/cm^2$, a coloration on a fair skin, defined in the (L*, a*, b*) calorimetric measuring system by a ratio Δa*/Δb*, ranging from 0.5 to 3, such as, for example, ranging from 0.8 to 2.

According to the (L*, a*, b*) calorimetric measuring system:

L* represents the luminance or clarity, a* represents the red-green axis (−a*=green, +a*=red) and b* represents the yellow-blue axis (−b*=blue, +b*=yellow). Thus, a* and b* express the shade of the skin. ΔL* relates to the darkening of the color: the more negative the ΔL*, the darker the color, where, in the present case, ΔL*=L* uncolored skin−L* colored skin.

The ratio Δa*/Δb* reflects the red/yellow balance and thus the shade, where, in the present case:

Δa*=a* uncolored skin−a* colored skin, and

Δb*=b* uncolored skin−b* colored skin.

As used herein, the term "fair skin" is understood to mean an untanned skin whose calorimetric characteristics may be defined by its ITA angle as defined in the publication by A. Chardon et al. "Skin Color Typology and Suntanning Pathways" presented at the 16th IFSCC congress, Oct. 8–10, 1990, New York, and in Int. J. Cosm. Sci. 13 191–208 (1991), the disclosures of which are incorporated herein by reference. Fair skin, as defined in this classification, has an ITA angle of between 35 and 55.

Compositions according to the present invention may be prepared, for example, according to techniques that are well-known to those skilled in the art, such as, for example, those intended for preparing oil-in-water or water-in-oil emulsions.

Compositions according to the present invention may be in a form chosen from simple and complex (such as, for example, O/W, W/O, O/W/O, and W/O/W) emulsions, such as, for example, creams and milks, gels, cream-gels, powders, and solid tubes, and may optionally be packed as an aerosol and may be in a form chosen from, for example, a mousse and a spray.

According to certain embodiments, the compositions according to the invention may be in the form of a water-in-silicone emulsion, and the organomodified silicone used may be chosen from, for example, oxyalkylenated (such as, for example, oxyethylenated and oxypropylenated) groups, such as, for example, those of formula (I) and (II) defined above.

The compositions according to the invention may further comprise at least one agent for at least one of artificially tanning and bronzing the skin (self-tanning agents), such as, for example, dihydroxyacetone (DHA).

According to certain embodiments, cosmetic compositions according to the present invention may optionally further comprise at least one screening agent chosen from UVA-active and UVB-active organic screening agents. These screening agents may be chosen, for example, from anthranilates; cinnamic derivatives; dibenzoylmethane derivatives; salicylic derivatives; camphor derivatives; triazine derivatives such as those disclosed in patent applications U.S. Pat. No. 4,367,390, EP 863,145, EP 517,104, EP 570 838, EP 796 851, EP 775 698, EP 878 469 and EP 933 376, the disclosures therein directed to said screening agents are incorporated herein by references; benzophenone derivatives; β,β'-diphenylacrylate derivatives; benzotriazole derivatives; benzimidazole derivatives; imidazolines; bis-benzazolyl derivatives such as those disclosed in patents EP 669 323 and U.S. Pat. No. 2,463,264, the disclosures therein directed to said screening agents are incorporated herein by reference; p-aminobenzoic acid (PABA) derivatives; methylenebis (hydroxyphenylbenzotriazole) derivatives as disclosed in patent applications U.S. Pat, Nos. 5,237,071, 5,166,355, GB 2 303 549, DE 19 726 184 and EP 893 119, the disclosures therein directed to said screening agents are incorporated herein by references; screening polymers and screening silicones such as those disclosed in particular in patent application WO 93/04665, the disclosure therein directed to said screening agents is incorporated herein by references; dimers derived from a -alkylstyrene, such as those disclosed in patent application DE 19 855 649, the disclosure therein directed to said screening agents is incorporated herein by references; 4,4-diarylbutadiene derivatives such as those disclosed in patent applications EP 0 967 200 and DE 19 755 649, the disclosures therein directed to said screening agents are incorporated herein by references.

According to certain embodiments, cosmetic compositions according to the present invention may optionally further comprise at least one of pigments and nanopigments (which have an average size of a primary particles typically ranging from 5 nm to 100 nm, such as, for example, from 10 nm to 50 nm) of coated and uncoated metaloxides. For example, the composition may optionally further comprise at least one of titaniumoxide (amorphous or crystallized in at least one of rutile and anatase forms), iron oxide, zinc oxide, zirconium oxide, and cerium oxide nanopigments, which are all UV stabilizers that are well known per se. Conventional coating agents, such as at least one alumina and aluminium stearate, also can be optionally used in the compositions according to the present invention. Such coated or uncoated metal oxide nanopigments are disclosed in particular in patent applications EP-A-0 518 772 and EP-A-0 518 773, the disclosures of which directed to said nanopigments is incorporated herein by reference.

According to certain embodiments, cosmetic compositions according to the present invention may optionally further comprise at least one conventional cosmetic adjuvant chosen in from, for example, fatty substances, organic solvents, thickeners, softeners, opacifiers, stabilizers, emollients, antifoams, moisturizers, fragrances, preserving agents, polymers, fillers, sequestering agents, propellants, acidifying and basifying agents, and other ingredient usually used in and/or suitable for use in cosmetics, such as, for example, those used for and/or suitable for use for manufacturing antisun compositions in the form of emulsions.

The fatty substance may be chosen from oils, waxes, and mixtures thereof, and they also be chosen from fatty acids, fatty alcohols, and fatty acid esters. The oils may be chosen from animal, plant, mineral, and synthetic oils, such as, for example, from liquid paraffin, volatile and non-volatile silicone oils, isoparaffins, polyolefins, fluoro oils, and perfluoro oils. Similarly, the waxes may be chosen from animal, fossil, plant, mineral, and synthetic waxes.

Among the organic solvents which may be mentioned are lower alcohols and polyols.

According to certain embodiments, a composition according to the invention comprises at least one polyhydroxylated solvent in an amount of at least 5% by weight relative to the weight of the composition. The at least one polyhydroxylated solvent may be chosen from glycols and glycolethers, such as, for example, ethylene glycol, propylene glycol, butylene glycol, dipropylene glycol, and diethyleneglycol. According to certain embodiments, a compositions according to the invention comprises a mixture of at least three different polyhydroxylated solvents such as, for example, a mixture comprising propylene glycol, butylene glycol, dipropylene glycol.

Needless to say, a person skilled in the art will take care to select this/these optional additional compound(s) and/or the amounts thereof such that the advantageous properties, in particular the water resistance and stability, intrinsically associated with the emulsions in accordance with the invention are not, or are not substantially, adversely affected by the addition(s) envisaged.

When a composition of the invention is an emulsion, the aqueous phase of this emulsion may comprise a nonionic vesicular dispersion prepared according to known processes, such as, for example, as disclosed in Bangham, Standish and Watkins, J. Mol. Biol. 13, 238(1965), French Patent 2,315, 991, French Patent 2,416,008, the disclosures of which directed to vesicular dispersions and emulsions are incorporated herein by reference.

According to certain embodiments, when the cosmetic composition according to the invention is used for coloring the human epidermis, it may be in the form of at least one of suspensions and dispersion sin at least one of at least one solvent and at least one fatty substance. The composition may be in the form of one of a nonionic vesicular dispersion and an emulsion, such as, for example, an oil-in-water emulsion, such as, as a further example, one of a cream and a milk. The composition may also be in the form of one of an ointment, a gel, a cream-gel, a solid tube, a powder, a stick, an aerosol mousse, and a spray.

As discussed above, according to certain embodiments, the present invention is directed to the use of an emulsion according to the invention to manufacture a cosmetic composition for coloring the at least one of the skin and the hair.

According to certain embodiments, the present invention is directed to the use of an organomodified silicone in the manufacture of a cosmetic or dermatological emulsion comprising at least one flavylium salt which is unsubstituted in position 3, and which is substituted with at least one radical chosen from hydroxyl and alkoxy radicals, in order to improve the stability and cosmetic acceptability of the composition.

The following specific but in non-limiting examples illustrating the invention will now be given.

EXAMPLE 1

An extract of *Sorghum bicolor* with a titre of 20–30% apigeninidine chloride was prepared according to the following preparation process:

An extract from the leaves of *Sorghum bicoloris* was obtained by aqueous-alcoholic (95° ethanol) extraction in acidic medium (0.2% HCl) at an extraction temperature of 35° C. with a ratio of the volume of solvent to the mass of *Sorghum bicolor* leaves of 15. The Sorghum plant extract was oven-dried for 24 hours at 40° C. and screened at 200 μm.

The yield for this extraction was 22.42% colorant matter.

The titre for the extract thus obtained was 21% by weight of a pigeninidine chloride.

This example is intended to show, firstly, the stability on storage of a composition A according to the invention containing the extract of *Sorghum bicolor* in an emulsion (water-in-silicone) support containing an organomodified silicone, compared with composition B containing the extract of *Sorghum bicolorin* an emulsion (oil-in-water) support not containing organomodified silicone.

This example is intended to show, secondly, that composition A in accordance with the present invention, applied to fair skin, rapidly gives a coloration close to that of a natural tan, in contrast with an emulsion C of the prior art containing an organomodified silicone but containing DHA instead of the extract of *Sorghum bicolor*.

The Inventors prepared the following compositions:

| Composition A (invention): | |
| --- | --- |
| Polydimethyl/methyl siloxane POE/POP (396/4)(EO/PO 18/18) A 10% D5 | 10 g |
| Cyclopentadimethylsiloxane | 12.5 g |
| Mixture of natural tocopherols/soybean oil | 0.1 g |
| Sodium chloride | 2 g |
| Propylene glycol | 23 g |
| Butylene glycol | 5 g |
| Dipropylene glycol | 10 g |
| Demineralized water | 35.959 g |
| extract of Sorghum bicolor as prepared above | 0.7 g |
| Trisodium citrate | 0.535 g |
| Citric acid | 0.206 g |

| Composition B (not according to the invention) | |
| --- | --- |
| Mixture of glyceryl mono-distearate/oxy-ethylenatedcetylstearyl alcohol | 3 g |
| Stearyl alcohol | 2.5 g |
| Mixture of glyceryl mono-distearate/poly-ethyleneglycol stearate | 2.5 g |
| Mixture of para-hydroxybenzoates/2-phenoxy-ethanol | 0.5 g |
| Polyisobutylene | 1 g |
| Di-tert-butyl-4-hydroxytoluene | 0.5 g |
| C12/C15 alkyl benzoate | 3 g |
| Extract of Sorghum bicolor as prepared above | 0.7 g |
| 1,3-butylene glycol | 5 g |
| Propylene glycol | 10 g |
| Liquid petroleum jelly | 5 g |
| DL-a-tocopheryl acetate | 0.25 g |
| Demineralized water | 66.05 g |

Formulations A and B were first examined macroscopically and then microscopically in white light and polarized light after subjecting them to a storage time of 2 months at room temperature and in an oven at 45° C.

It was observed that after storage for 2 months composition B was unstable and showed filaments, red precipitates, and air bubbles, while composition A maintained its initial appearance.

Comparison With an Emulsion Containing DHA:

The inventors prepared the following composition:

| Composition C (not according to the invention): | |
| --- | --- |
| Polydimethyl/methyl siloxane POE/POP (396/4)(EO/PO 18/18) at 10% D5 | 10 g |
| Cyclopentadimethylsiloxane | 12.5 g |
| Mixture of natural tocopherols/soybean oil | 0.1 g |
| Dihydroxyacetone (DHA) | 4 g |
| Sodium chloride | 2 g |
| Propylene glycol | 23 g |
| Butylene glycol | 5 g |
| Dipropylene glycol | 10 g |
| Trisodium citrate | 0.535 g |
| Citric acid | 0.206 g |
| Demineralized water | 32.649 g |

Compositions A and C were applied in an amount of 2 mg/cm$^2$ to an area of 7×4.5 cm$^2$ delimited on the back of 6 volunteers whose skin color, characterized by the ITA angle, was between 35 and 55.

The following five series of calorimetric measurements were taken using a Minolta CR-300 calorimeter:

1) before applying the composition,
2) 30 minutes after the application,
3) 2 hours after application,
4) 4 hours after application,
5) 5 hours after application.

The results are expressed in the (L*, a*, b*) system in which L* represents the luminance, a* represents the red-green axis (−a*=green, +a*=red) and b* represents the yellow-blue axis (−b*=blue, +b*=yellow). Thus, a* and b* express the shade of the skin.

To evaluate the intensity of the coloration, the important value is the ΔL* which reflects the darkening of the color: the more negative the ΔL*, the darker the color, with:

ΔL*=L* uncolored skin L* colored skin.

The results obtained are collated in Table(I) below:

TABLE (I)

| | Composition A (invention) ΔL* | Composition C (not according to the invention) ΔL* |
| --- | --- | --- |
| 30 minutes | −9.8 | −0.4 |
| 2 hours | −8.3 | −1.1 |
| 4 hours | −8.1 | −2.5 |
| 5 hours | −8.7 | −2.6 |

It was thus found that 30 minutes after application, composition C, which contains DHA as skin-coloring agent, gave the skin only a very faint coloration (ΔL*=−0.4), since the DHA had insufficient time to act. On the other hand, composition A according to the invention had already given the skin a significant coloration (ΔL*=−8.2).

Composition C containing DHA did not give after 30 minutes a darkening comparable to that of composition A, which furthermore had a constant coloration shade for 5 hours.

What is claimed is:

1. An emulsion, comprising (a) at least one aqueous phase;

(b) at least one fatty phase; and (c) at least one flavylium salt which is unsubstituted in position 3, substituted with at least one radical chosen from hydroxyl and alkoxy radicals, and present in an amount effective for obtaining a darkening of skin.

2. The emulsion according to claim 1, wherein the emulsion comprises the at least one flavylium salt in an amount effective for obtaining, 30 minutes after application of the emulsion to a fair skin in an amount of 2 mg/cm$^2$, the darkening of the skin characterized in a L*a*b* calorimetric measuring system by a ΔL* ranging from −0.5 to −20.

3. The emulsion according to claim 1, wherein the emulsion comprises the at least one flavylium salt in an amount effective for obtaining, 30 minutes after application of the emulsion to a fair skin in an amount of 2 mg/cm$^2$, the darkening of the skin color by a coloration on the fair skin, defined in a (L*, a*, b*) calorimetric measuring system by a ratio Δa*/Δb* ranging from 0.5:1 to 3:1.

4. The emulsion according to claim 1, further comprising at least one organomodified silicone.

5. The emulsion according to claim 4, wherein said at least one organomodified silicone is chosen from:

(1) polyorganosiloxanes comprising oxyalkylenated groups;

(2) polyorganosiloxanes comprising alkoxylated groups;

(3) polyorganosiloxanes comprising anionic groups;

(4) polyorganosiloxanes comprising thiol groups;

(5) polyorganosiloxanes comprising anionic groups chosen from carboxylic anionic groups;

(6) polyorganosiloxanes comprising hydroxylated groups;

(7) polyorganosiloxanes comprising acyloxyalkyl groups;

(8) polyorganosiloxanes comprising at least one of substituted and unsubstituted amine groups;

(9) polyorganosiloxanes comprising hydroxyacylamino groups; and

(10) polyorganosiloxanes comprising optionally substituted aryl groups.

6. The emulsion according to claim 4, wherein the at least one organomodified silicone is chosen from polyorganosiloxanes of formulae (I) and (II) as follows:

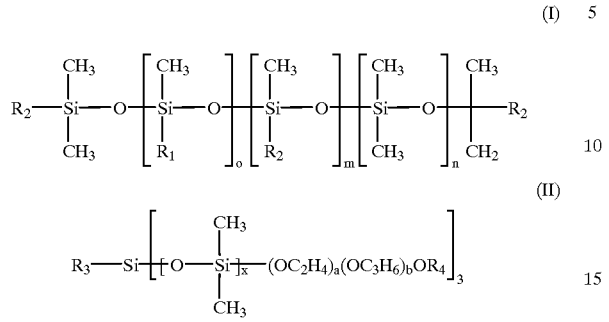

wherein:
- each $R_1$ is, independently, chosen from linear and branched $C_1$–$C_{30}$ alkyl and phenyl radicals;
- each $R_2$ is, independently, chosen from —$C_cH_{2c}$—(—O—$C_2H_4$)$_a$—(—O—$C_3H_6$)$_b$—(O—$C_4H_8$)$_d$—$R_5$;
- each $R_3$ and each $R_4$ is, independently, chosen from linear and branched $C_1$–$C_{12}$ alkyl radicals;
- each $R_5$ is, independently, chosen from a hydrogen atom, a hydroxyl radical, linear and branched alkyl radicals comprising from 1 to 12 carbon atoms, linear and branched alkoxy radicals comprising from 1 to 6 carbon atoms, linear and branched acyloxy radicals comprising from 2 to 12 carbon atoms, $NHCH_2CH_2COOM$, aminoalkyl optionally substituted on the amine, carboxy ($C_1$–$C_{30}$) acyl, optionally substituted phosphono groups, —O—CO—$(CH_2)_d$—$CO_2M$, —$NHCO(CH_2)_d$OH, and —$NH_3Y$;
- each M is, independently, chosen from hydrogen, Na, K, Li, $NH_4$, and organic amines;
- a is a number ranging from 0 to 50;
- b is a number ranging from 0 to 50;
- c is a number ranging from 0 to 4;
  with the proviso that a sum of a +b is greater than or equal to 1;
- d is a number ranging from 0 to 10;
- m is a number ranging from 0 to 20;
- n is a number ranging from 0 to 500;
- o is a number ranging from 0 to 20;
- x is a number ranging from 0 to 100; and
- Y is chosen from mineral and organic monovalent anions.

7. The emulsion according to claim 6, wherein at least one of the $R^3$ and $R^4$ radicals is chosen from a methyl radical.

8. The emulsion according to claim 4, wherein the at least one organomodified silicone is chosen from 2-hydroxyalkylsulphonate and 2-hydroxy-alkylthiosulphate.

9. The emulsion according to claim 4, wherein the at least one organomodified silicone is chosen from polyorganosiloxanes of formula (III) below:

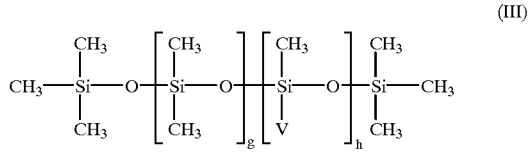

wherein:
V is chosen from radicals of the formula —$(R^1O)_e$—$R^2$—$(OR^3)_f$—COOM, wherein

- each $R^1$ and each $R^3$ is, independently, chosen from linear or branched alkylene radical comprising from 2 to 20 carbon atoms,
- each $R^2$ is, independently, chosen from linear and branched alkylene radical comprising from 1 to 50 carbon atoms and optionally comprising at least one hydroxyl group,
- e is a number chosen from 0 and 1,
- f is a number ranging from 0 to 200, and
- M is chosen from hydrogen, alkalimetal and alkaline-earth metals, $NH_4$, and quaternary ammonium groups;
- h is a number ranging from 1 to 1000; and
- g is a number ranging from 0 to 1000.

10. The emulsion according to claim 9, wherein M is chosen from mono-, di-, tri-, and tetra($C_1$–$C_4$ alkyl) ammonium groups.

11. The emulsion according to claim 9, wherein a sum of g+h ranges from 2 to 1000.

12. The emulsion according to claim 4, wherein the at least one organomodified silicone is chosen from polyorganosiloxanes of formula (IV) below:

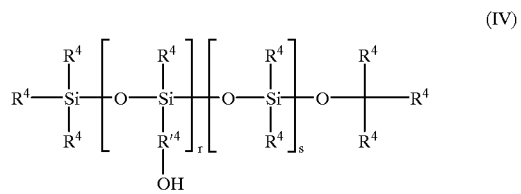

wherein:
- each $R^4$ is, independently, chosen from methyl and phenyl radicals, with the proviso that at least 60 mol % of the radicals $R^4$ are chosen from methyl,
- each $R'^4$ is, independently, chosen from divalent hydrocarbon-based $C_2$–$C_{18}$ alkylene chain units,
- r is a number ranging from 1 to 30, and
- s is a number ranging from 1 to 150.

13. The emulsion according to claim 4, wherein the at least one organomodified silicone is chosen from polyorganosiloxanes of formula (V):

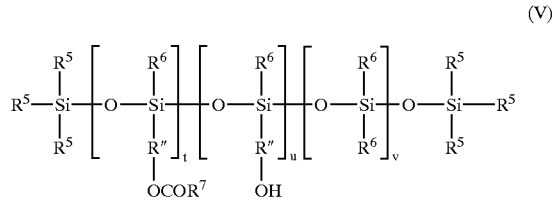

wherein:
- each $R^5$ is, independently, chosen from methyl, phenyl, —$OCOR_5$, and hydroxyl groups, with the proviso that not more than one of the radicals $R^5$ attached to one silicon atom is chosen from hydroxyl;
- each R" is, independently, chosen from linear and branched divalent hydrocarbon-based $C_2$–$C_{18}$ alkylene radicals;
- each $R^6$ is, independently, chosen from methyl and phenyl, with the proviso that at least 60 mol % of all of the radicals $R^5$ and $R^6$ are chosen from methyl groups;
- each $R^7$ is, independently, chosen from $C_8$–$C_{20}$ alkyl and alkenyl groups;

v is a number ranging from 1 to 120;

u is a number ranging from 1 to 30; and t is a number ranging from 0 to less than a value of 0.5 u,
with the proviso that a value of t+u ranges from 1 to 30, and
with the proviso that the polyorganosiloxanes of formula (V) may contain groups of the following formula:

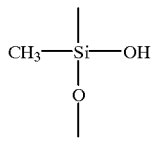

in a proportion not exceeding 15% of a sum of t+u+v.

14. The emulsion according to claim 4, wherein the at least one organomodified silicone is chosen from:

(a) polysiloxanes corresponding to formula (VI):

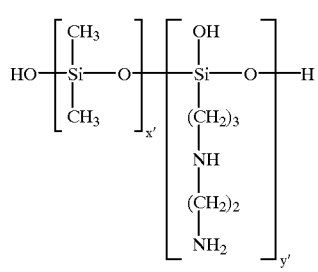

wherein x' and y' are integers chosen such that a number-average molecular weight of the polysiloxanes to formula (VI) ranges from 5000 to 500,000;

(b) cationic silicone polymers corresponding to formula (VII):

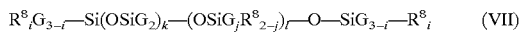

wherein:

G is chosen from a hydrogen atom and phenyl, OH, and $C_1$–$C_8$ alkyl groups, i is an integer ranging from 0 to 3, j is a number chosen from 0 and 1, k and l are numbers chosen such that a sum (k+l) ranges from 1 to 2000, wherein k is optionally chosen from a number ranging from 0 to 1999, and l is optionally chosen from a number ranging from 1 to 2000,
with the proviso that at least one of i and l are greater than or equal to 1, $R^8$ is chosen from monovalent radicals of formula —$C_qH_{2q}$L, wherein q is a number ranging from 2 to 8 and L is an optionally quaternized amine group chosen from groups:
—$NR^9$—$CH_2$—$CH_2$—$N(R^9)_2$,
—$N(R^9)_2$,
—$N^\oplus(R^9)_3A^-$, and
—$N^\oplus(R^9)$—$CH_2$—$CH_2$—$N^\oplus R^9H_2A^-$, wherein $R^9$ is chosen from hydrogen, phenyl, benzyl, and saturated monovalent hydrocarbon-based radicals, and $A^-$ is chosen from halide ions; and (c) cationic silicone polymers corresponding to formula (VIII):

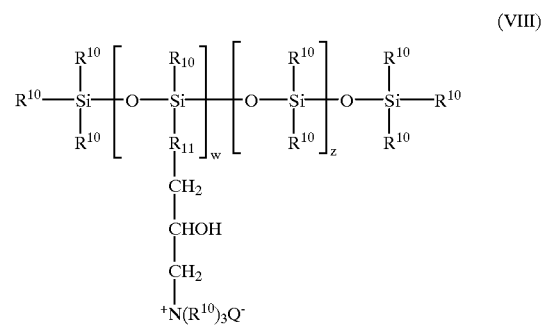

wherein:
each $R^{10}$ is, independently, chosen from monovalent hydrocarbon-based radicals comprising from 1 to 18 carbon atoms,
$R^{11}$ is chosen from divalent hydrocarbon-based radicals,
$Q^-$ is a halide ion,
w represents an average statistical value, and is chosen from a number ranging from 2 to 20, and
z represents an average statistical value, and is chosen from a number ranging from 20 to 200.

15. The emulsion according to claim 14, wherein the at least one organomodified silicone is chosen from formula (VII) and g is chosen from a methyl group.

16. The emulsion according to claim 14, wherein the at least one organomodified silicone is chosen from formula (VII) and the sum (k+l) ranges from 50 to 150.

17. The emulsion according to claim 14, wherein the at least one organomodified silicone is chosen from formula (VII) and k has a value ranging from 49 to 149.

18. The emulsion according to claim 14, wherein the at least one organomodified silicone is chosen from formula (VII) and l has a value ranging from 1 to 10.

19. The emulsion according to claim 14, wherein the at least one organomodified silicone is chosen from formula (VII) and $R^9$ is chosen from an alkyl radical comprising from 1 to 20 carbon atoms.

20. The emulsion according to claim 14, wherein the at least one organomodified silicone is chosen from formula (VIII) and $R^{10}$ is chosen from $C_1$–$C_{18}$ alkyl and $C_2$–$C_{18}$ alkenyl radicals.

21. The emulsion according to claim 14, wherein the at least one organomodified silicone is chosen from formula (VII) and $R^{10}$ is chosen from methyl.

22. The emulsion according to claim 14, wherein the at least one organomodified silicone is chosen from formula (VIII) and $R^{11}$ is chosen from $C_1$–$C_{18}$ alkylene and divalent $C_1$–$C_{18}$ alkyl radicals.

23. The emulsion according to claim 14, wherein the at least one organomodified silicone is chosen from formula (VIII) and $R^{11}$ is chosen from $C_1$–$C_8$, alkylenoxy radicals.

24. The emulsion according to claim 14, wherein the at least one organomodified silicone is chosen from formula (VIII) and w has a value ranging from 2 to 8.

25. The emulsion according to claim 14, wherein the at least one organomodified silicone is chosen from formula (VIII) and z has a value ranging from 20 to 50.

26. The emulsion according to claim 4, wherein the at least one organomodified silicone is present in an amount ranging from 0.1% to 40% relative to the total weight of the composition.

27. The emulsion according to claim 4, wherein the at least one organomodified silicone is present in an amount ranging from 0.5% to 20% relative to the total weight of the composition.

28. The emulsion according to claim 1, wherein the at least one flavylium salt is chosen from formula (1) below:

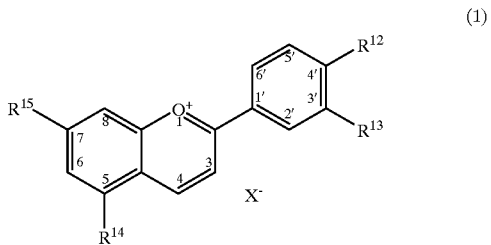

(1)

wherein:
- $R^{12}$ is chosen from an OH radical, and linear and branched, saturated and unsaturated $C_1$–$C_8$ alkoxy radicals;
- $R^{13}$, $R^{14}$, and $R^{15}$, which may be identical or different, are each chosen from H and $R^{12}$, with the proviso that at least one of the radicals $R^{12}$, $R^{13}$, $R^{14}$, $R^{15}$ is chosen from OH; and
- $X^-$ is chosen from organic and mineral anions.

29. The emulsion according to claim 28, wherein $X^-$ is chosen from halides and anions derived from organic acids.

30. The emulsion according to claim 28, wherein, in formula (1), $R^{12}$ is chosen from OH and $OCH_3$.

31. The emulsion according to claim 1, wherein the at least one flavylium salt is chosen from salts of the following:
4',5,7-trihydroxyflavylium,
3',4',7-trihydroxyflavylium,
4'-hydroxyflavylium,
4',7-dihydroxyflavylium,
3',4'-dihydroxyflavylium,
3',4'-dihydroxy-7-methoxyflavylium,
3',4',5,7-tetrahydroxyflavylium, and
3',4',5',5,7-pentahydroxyflavylium.

32. The emulsion according to claim 31, wherein the salts are chloride salts.

33. The emulsion according to claim 1, wherein the at least one flavylium salt is obtained at least one of synthetically, from a plant extract, and from an enriched plant extract.

34. The emulsion according to claim 1, wherein the at least one flavylium salt is chosen from 4',5,7-trihydroxyflavyliumchloride.

35. The emulsion according to claim 1, wherein the at least one flavylium salt is chosen from synthetically formed 4',5,7-trihydroxyflavyliumchloride.

36. The emulsion according to claim 1, wherein the at least one flavylium salt is chosen from 4',5,7-trihydroxyflavyliumchloride in the form of a plant extract.

37. The emulsion according to claim 36, wherein the plant extract is a plant extract obtained from at least one of leaves of *Sorghum caudatum;* stems, seeds, and leaves of *Sorghum bicolor,* petals of *Gesneria fulgens;* and at least one species chosen from Blechumprocerum and Sorghum in combination with Colletotrichumgraminicola.

38. The emulsion according to claim 36, wherein the plant extract is an extract of *Sorghum bicolor* obtained by an acidic aqueous-alcoholic extraction at an extraction temperature ranging from 30° C. to 40° C. with a ratio of the volume of solvent to the mass of *Sorghum bicolor* leaves ranging from 10 to 30.

39. The emulsion according to claim 38, wherein the extract of *Sorghum bicolor* has a titre ranging from 0.05% to 50% by weight of 4',5,7-trihydroxyflavylium chloride.

40. The emulsion according to claim 1, wherein the at least one flavylium salt is present in an amount ranging from 0.0001% to 10% relative to the total weight of the emulsion.

41. The emulsion according to claim 1, wherein the at least one flavylium salt is present in an amount ranging from 0.001% to 5% by weight relative to the total weight of the emulsion.

42. The emulsion according to claim 1, wherein the emulsion comprises a water-in-silicone emulsion.

43. The emulsion according to claim 5, wherein the emulsion comprises a water-in-silicone emulsion.

44. The emulsion according to claim 6, wherein the emulsion comprises a water-in-silicone emulsion.

45. The emulsion according to claim 1, wherein the emulsion has a form chosen from at least one of creams, milks, gels, cream-gels, powders, and solid tubes.

46. The emulsion according to claim 1, wherein the emulsion is configured an aerosol.

47. The emulsion according to claim 46, wherein the emulsion has a form chosen from at least one of a mousse and a spray.

48. The emulsion according to claim 1, wherein the emulsion comprises at least one at least one polyhydroxylated solvent in an amount of at least 5% by weight relative to the weight of the composition.

49. The emulsion according to claim 48, wherein the at least one polyhydroxylated solvent is chosen from glycols and glycol ethers.

50. The emulsion according to claim 48, wherein the at least one polyhydroxylated solvent is chosen from ethylene glycol, propylene glycol, butylene glycol, dipropylene glycol, and diethylene glycol.

51. The emulsion according to claim 48, wherein the emulsion comprises a mixture of at least three different polyhydroxylated solvents.

52. The emulsion according to claim 48, wherein the emulsion comprises a mixture comprising propylene glycol, butylene glycol, and dipropylene glycol.

53. A composition intended for artificially coloring skin, comprising
   (a) at least one aqueous phase;
   (b) at least one fatty phase; and
   (c) at least one flavylium salt which is unsubstituted in position 3, substituted with at least one radical chosen from hydroxyl and alkoxy radicals.

54. A method of manufacturing a cosmetic composition comprising preparing an emulsion, comprising
   (a) at least one aqueous phase;
   (b) at least one fatty phase; and
   (c) at least one flavylium salt which is unsubstituted in position 3, substituted with at least one radical chosen from hydroxyl and alkoxy radicals, wherein the composition is configured to provide artificial coloration of skin.

55. The method according to claim 54, wherein the at least one flavylium salt is obtained at least one of synthetically, from a plant extract, and from an enriched plant extract.

56. The method according to claim 54, wherein the coloration is close to that of a natural tan.

57. The method according to claim 54, wherein the at least one flavylium salt is present in an amount effective for obtaining, 30 minutes after application to a fair skin, a darkening of the skin characterized in a L*a*b* calorimetric measuring system by a ΔL* ranging from −0.5 to −20.

58. The method according to claim 54, wherein the at least one flavylium salt is present in an amount effective for obtaining, 30 minutes after application to the skin in an amount of 2 mg/cm$^2$, a coloration on a fair skin, defined in the (L*,a*,b*) calorimetric measuring system by a ratio Δa*/Δb* ranging from 0.5:1 to 3:1.

59. The method of claim 54, wherein the emulsion further comprises at least one organomodified silicone.

60. A cosmetic treatment process for skin, comprising:
giving the skin an artificial coloration, said process further comprising applying to the skin an effective amount of an emulsion comprising
(a) at least one aqueous phase;
(b) at least one fatty phase; and
(c) at least one flavylium salt which is unsubstituted in position 3, substituted with at least one radical chosen from hydroxyl and alkoxy radicals.

61. The process according to claim 60, wherein the emulsion further comprises at least one organomodified silicone.

62. The process according to claim 60, wherein the coloration is close to that of a natural tan.

63. The process according to claim 60, wherein the at least one flavylium salt is obtained at least one of synthetically, from a plant extract, and from an enriched plant extract.

64. The process according to claim 60, wherein the emulsion comprises the at least one flavylium salt in an amount effective for obtaining, 30 minutes after application of the emulsion to a fair skin in an amount of 2 mg/cm$^2$, a darkening of the skin characterized in a L*a*b* calorimetric measuring system by a ΔL* ranging from −0.5 to −20.

65. The process according to claim 60, wherein the emulsion comprises the at least one flavylium salt in an amount effective for obtaining, 30 minutes after application to the skin in an amount of 2 mg/cm$^2$, a coloration on a fair skin, defined in the (L*,a*,b*) calorimetric measuring system by a ratio Δa*/Δb* ranging from 0.5:1 to 3:1.

66. A cosmetic treatment process for skin, comprising:
applying to an emulsion intended for artificially coloring the skin, comprising
(a) at least one aqueous phase;
(b) at least one fatty phase; and
(c) at least one flavylium salt which is unsubstituted in position 3, substituted with at least one radical chosen from hydroxyl and alkoxy radicals.

67. A method of giving skin an artificial coloration, comprising:
using at least one at least one flavylium salt which is unsubstituted in position 3, substituted with at least one radical chosen from hydroxyl and alkoxy radicals, and using at least one organomodified silicone in an emulsion that is at least one of a cosmetic and a dermatological emulsion; and
applying said composition to the skin.

68. The method according to claim 67, wherein the coloration is close to that of a natural tan.

69. The method according to claim 67, wherein the emulsion is intended for artificially coloring the skin.

70. A method of giving skin an artificial coloration, comprising:
using at least one at least one flavylium salt which is unsubstituted in position 3, substituted with at least one radical chosen from hydroxyl and alkoxy radicals, and
using at least one organomodified silicone, in a composition that is at least one of a cosmetic and a dermatological composition; and
applying said composition to the skin.

71. The method according to claim 67, wherein the coloration is close to that of a natural tan.

72. The method according to claim 67, wherein the composition is intended for artificially coloring the skin.

73. A composition comprising at least one an organomodified silicone and at least one flavylium salt which is unsubstituted in position 3 and substituted with at least one radical chosen from hydroxyl and alkoxy radicals; wherein the composition comprises at least one of a cosmetic and a dermatological emulsion; and the composition is configured to provide a coloration of the skin, to provide the composition with good physical stability, and to be cosmetically pleasant.

74. A method of artificially coloring skin, comprising applying to the skin a composition comprising at least one an organomodified silicone and at least one flavylium salt which is unsubstituted in position 3 and substituted with at least one radical chosen from hydroxyl and alkoxy radicals; wherein the composition comprises at least one of a cosmetic and a dermatological emulsion; and the composition is configured to provide a coloration of the skin, to provide the composition with good physical stability, and to be cosmetically pleasant.

75. A method of manufacturing a composition, comprising including an organomodified silicone in the composition, wherein the composition is at least one of a cosmetic and a dermatological emulsion; the composition comprises at least one at least one flavylium salt which is unsubstituted in position 3 and substituted with at least one radical chosen from hydroxyl and alkoxy radicals; and the composition is configured to provide a coloration of the skin, to provide the composition with good physical stability, and to be cosmetically pleasant.

76. The method according to claim 75, wherein the composition is configured to provide upon application to the skin an immediate coloration of the skin.

77. The method according to claim 75, wherein the composition is configured to provide upon application to the skin a coloration of the skin within 30 minutes.

* * * * *

UNITED STATES PATENT AND TRADEMARK OFFICE
CERTIFICATE OF CORRECTION

PATENT NO.    : 6,511,656 B2
DATED         : January 28, 2003
INVENTOR(S)   : Didier Candau et al.

It is certified that error appears in the above-identified patent and that said Letters Patent is hereby corrected as shown below:

Column 16,
Lines 38 and 45, "calorimetric" should read -- colorimetric --.

Column 21,
Line 56, "*bicolor*," should read -- *bicolor*; --.

Column 22,
Line 18, after "configured" insert -- as --.
Line 23, delete "at least one" (first occurrence).
Line 64, "calorimetric" should read -- colorimetric --.

Column 23,
Lines 3, 28 and 34, "calorimetric" should read -- colorimetric --.
Line 46, delete "at least one" (first occurrence).

Column 24,
Line 5, delete "at least one" (first occurrence).
Lines 17 and 29, delete "an".
Line 41, delete "at least one" (first occurrence).

Signed and Sealed this

Twenty-sixth Day of August, 2003

JAMES E. ROGAN
*Director of the United States Patent and Trademark Office*